United States Patent [19]

Garnett et al.

[11] 4,432,889

[45] Feb. 21, 1984

[54] HETEROGENEOUS CATALYST

[75] Inventors: John L. Garnett, Longueville; Mervyn A. Long, St. Ives; Ronald G. Levot, Oyster Bay, all of Australia

[73] Assignee: Unisearch Limited, Kensington, Australia

[21] Appl. No.: 225,409

[22] Filed: Feb. 6, 1981

[51] Int. Cl.$^3$ .............................................. B01J 31/24
[52] U.S. Cl. ..................................... 502/5; 502/155; 502/165; 502/166
[58] Field of Search ............... 252/429 R, 431 P, 427, 252/430

[56]  References Cited

U.S. PATENT DOCUMENTS 4,179,401 12/1979 Garnett et al. .................. 252/429 R
4,228,035 10/1980 Gray et al. .................. 252/431 P X
4,258,206 3/1981 Pittman et al. .............. 252/431 P X Primary Examiner—Patrick Garvin Attorney, Agent, or Firm—Michael J. Striker

[57]  ABSTRACT

A heterogeneous catalyst formed by the steps of:
(a) irradiating an organic macromolecular substrate or a metal substrate with ionizing or U.V. radiation in the presence of a monomer selected from the group comprising o-, m-, or p- styryl diphenyl phosphine or o-, m-, or p- phenyl acrylyl diphenyl phosphine to graft the monomer to the substrate, and
(b) reacting the graft copolymer with a homogeneous catalyst selected from the group consisting of catalytic metal salts and catalytic organometallic complexes such that the monomer-substrate conjugate becomes a ligand of the catalyst.

These catalysts have particular activity in hydrogenation reactions, hydroformylation reactions, isomerization reactions, cracking reactions and dehydrogenation reactions of organic compounds.

19 Claims, No Drawings

HETEROGENEOUS CATALYST

The present invention relates to an improved heterogeneous catalyst and to a process for the production thereof.

In Australian Pat. No. 492,175 corresponding to U.S. Pat. No. 4,179,401 there is disclosed a class of heterogeneous catalyst formed by grafting one of a defined class of monomers to a substrate and reacting the monomer-substrate conjugate with a homogeneous catalyst selected from the group comprising catalytic metal salts and catalytic organometallic complexes such that the monomer-substrate conjugate becomes a ligand of the catalyst.

It is known that heterogeneous catalysts can be useful in a variety of chemical reactions in which homogeneous catalytic metal salts and organometallic complexes are known to have catalytic activity. Without limit to the scope of the utility of the catalysts according to this invention it is known that these catalysts show activity in hydrogenation reactions, hydroformylation reactions, isomerisation reactions, cracking reactions and dehydrogenation reactions in respect of organic molecules.

The present invention relates to an improved class of monomers which may be used in the process according to Australian Pat. No. 492,175 and which in addition may be grafted to a substrate using U.V. radiation whether ionising or not.

The present invention consists in a process for the production of a heterogeneous catalyst comprising the steps of:

(a) irradiating an organic macromolecular substrate or a metal substrate with ionising or ultra violet radiation in the presence of a monomer selected from the group consisting of o-, m-, or p-styryl diphenyl phosphine and o-, m- or p-phenyl acrylyl diphenyl phosphine, to graft the monomer to the substrate, and (b) reacting the graft copolymer with a homogeneous catalyst selected from the group consisting of catalytic metal salts and catalytic organometallic complexes such that the monomer-substrate conjugate becomes a ligand of the catalyst.

In a further aspect the present invention consists in a heterogeneous catalyst comprising an organic macromolecular substrate or a metal substrate having grafted thereon a monomer selected from the group consisting of o-, m- or p-styryl diphenyl phosphine and o-, m-, or p-phenyl acryl diphenyl phosphine, this monomer-substrate conjugate being a ligand of a homogeneous catalyst selected from the group consisting of catalytic metal salts and catalytic organometallic complexes.

The homogeneous catalysts are preferably the catalytic metal salts and organometallic complexes of metals selected from the group consisting of Ruthenium, Rhodium, Palladium, Osmium, Iridium, and Platinum.

The process according to the present invention has the advantages that the monomer may be grafted to a substrate using either ionising radiation or non-ionising U.V. radiation and that the graft yield is much higher for a given radiation dose using the present process as compared with the process of the earlier patent. This latter advantage means that lower radiation doses may be used to produce a given level of graft while reducing the possibility of radiation damage to the substrate.

As many of the homogeneous catalysts used in the production of heterogeneous catalysts are extremely expensive it is vital that in use the homogeneous catalyst will not become detached from the monomer-substrate conjugate. The heterogeneous catalysts according to the present invention appear to be more stable than previously known heterogeneous catalysts, including those known from Australian Pat. No. 492,175.

The preferred substrates for use in the process according to this invention include polyethylene, polypropylene, polystyrene, polyvinyl chloride, cellulose and wool. While these materials are preferred as substrates a wide variety of other natural and synthetic organic polymers may also be used. Macromolecular materials which are not strictly polymeric may also be used as substrates, these include materials such as cellulose and proteins. The substrate may be used in the form of a film or a powder or any other form which provides sufficient surface area for the catalytic activity of the material to be sufficient for the particular reaction conditions. The substrate may alternatively be a metal such as copper, zinc, aluminium, iron or the like.

The monomer is most preferably p-styryl diphenyl phosphine although the other monomers referred to may be used to carry out the invention. The monomers are preferably grafted to the substrate with $\gamma$ radiation or U.V. radiation. If $\gamma$ radiation is used to induce grafting the radiation dose is preferably from $0.01 \times 10^6$ rad to $10 \times 10^6$ rad at preferred dose rates of from $0.001 \times 10^6$ rad/hr to $5 \times 10^6$ rad/sec., most preferred doses are from $0.5 \times 10^6$ rad to $5 \times 10^6$ rad at most preferred dose rates of from $0.01 \times 10^6$ rad/hr to $0.05 \times 10^6$ rad/hr. For U.V. induced grafting exposure times under a high pressure mercury 90 W (Phillips) lamp of from 1 to 100 hours were preferred with the sample distanced 30 cm. from the lamp.

It is very highly preferred that a suitable radical forming sensitiser, such as benzoin ethyl ether or biacetyl, be used when U.V. induced grafting is being undertaken. It is believed that the radicals formed as the sensitiser absorbs U.V. radiation can diffuse to a polymer site and abstract a hydrogen atom to form a grafting site. The sensitiser is preferably present in an amount of from 0.1% to 5% by volume of the reaction mixture. There is of course no requirement for such a sensitiser when the grafting is induced by ionising radiation.

If a solvent is used for the monomer during the grafting step it is preferably capable of swelling the substrate when the substrate is an organic polymer. This is particularly advantageous where a sensitiser is being used to enhance U.V. grafting of the monomer.

The homogeneous catalyst for attachment to the monomer-substrate conjugate could be any one of a wide variety of metal based catalysts selected from the group comprising metal salts and organo-metallic complexes. The so called "Wilkinson" catalysts (see J. A. Osborn, F. H. Jardine, J. F. Young and G. Wilkinson J. Chem. Soc. A 1966, 1711) are particularly suitable.

Hereinafter given by way of example only are preferred embodiments of the present invention.

In the following experiments polypropylene film (ex Shell) was isotactic, doubly oriented film (2.5×3.75×0.005 cm) and contained calcium stearate (0.1% by weight) and an antioxidant (0.1% by weight). Polypropylene and polyvinyl chloride powders (Ex ICI) were used as supplied and contained no additives P.V.C. film was prepared from the above P.V.C. powder. Polystyrene beads (ex Strem Chemicals) were 20% cross linked with divinyl benzine. For the U.V. studies a high pressure 90 W (Phillips) lamp was used. Irradiations were performed in lightly stoppered pyrex tubes, solvent being added first, followed by additive or a concentrated solution of additive in solvent, then monomer to make up a total volume of 20 ml. The trunk polymer was then immersed in the grafting solutions. After irradiation the polymer was treated as described in J. L. Garnett and N. T. Yen, Aust. J. Chem 32, 585 (1979).

For heterogenisation similar procedures were used to those reported in H. Barker, J. L. Garnett, R. S. Kenyon, R. Levot, M. S. Liddy and M. A. Long, Proc. 6th Intl. Congr. Catalysis, London, The Chemical Society, P. 551 (1977) and H. Barker, J. L. Garnett, R. Levot and M. A. Long, Proc. 2nd Intl. Conf. on P.V.C., Lyon, 76 (1976).

Table 1 set out hereunder shows the Gamma ray and U.V. grafting of p-styryl diphenyl phosphine to P.V.C. film. It can be seen that the monomer grafts efficiently with both U.V. and gamma sources. The inclusion of acid does not increase any of the gamma ray grafting yields though improvement is shown in some cases with acid and 1% divinyl benzene. Divinyl benzene or analagous cross linking agents, typically poly functional acrylates, are added not only to enhance the grafting yield but also to provide a more reactive monomer-substrate conjugate.

TABLE 1

Gamma ray and U.V. grafting of p-styryl diphenyl phosphine to polyvinyl chloride film[a].

| Method | Monomer (% v/v) | O | Graft (%) 0.1MH$_2$SO$_4$ | 0.1MH$_2$SO$_4$ + 1% D.V.B.[d] |
|---|---|---|---|---|
| b | 14 | 29 | 25 | 36 |
|   | 21 | 43 | 31 | 39 |
|   | 28 | 48 | 35 | 52 |
|   | 35 | 45 | 40 | 57 |
|   | 50 | 33 | 33 | 44 |
| UV[c] | 29 | — | 19 |   |

[a]In solvent dioxan/methanol (3/2 v/v).
[b]Radiation dose of 1.5 × 10$^6$ rad at 0.021 × 10$^6$ rad/hr.
[c]Benzoin ethyl ether (1% w/w) in irradiations at 30 cm for 41 hrs.
[d]1% (v/v) divinyl benzene.

Table 2 shows a representative group of monomer-substrate conjugates.

TABLE 2

Preparation of copolymers as reagent supports by photosensitized and radiation grafting[a]

| Support No. | Radiation | Grafting mixture | Wt (g) | Wt recovered (g) | Graft (%) |
|---|---|---|---|---|---|
| 1 | 4.0[b] | p-Styryl diphenyl phosphine | 5.7 | | |
|   |   | Polypropylene | 5.0 | 5.65 | 13[d] |
|   |   | Benzene | 13.2 | | |
| 2 | 2.5 | p-Styryl diphenyl phosphine | 5.0 | | |
|   |   | Polystyrene | 5.0 | 7.25 | 45 |
|   |   | Dioxan/methanol (3/2, v/v) | 11.2 | | |
| 3 | 5.0 | Vinyl diphenyl phosphine | 20.0 | | |
|   |   | Polyvinyl chloride | 20.0 | 20.4 | 2[d] |
|   |   | Dioxan/methanol (1/7, v/v)[c] | 131.0 | | |
| 4 | 1.5 | p-Styryl diphenyl phosphine | 40.0 | | |
|   |   | Polyvinyl chloride | 20.0 | 24.6 | 23 |
|   |   | Dioxan/methanol (3/2, v/v) | 187.0 | | |
| 5 | 4.0 | p-Nitrostyrene | 12.6 | | |
|   |   | Polypropylene | 20.0 | 20.4 | 2 |
|   |   | Methanol[c] | 142.0 | | |
| 6 | UV | p-Styryl diphenyl phosphine | 7.5 | | |
|   |   | Polystyrene | 5.0 | 5.75 | 15[d] |
|   |   | Dioxan/methanol (3.2, v/v) | 23.4 | | |
|   |   | Benzoin ethyl ether | 0.5 | | |

[a]All polymers used were powders with dose rate of 0.040 × 10$^6$ rad/hr except for support nos. 3,5,6 where 0.021 × 10$^6$ rad/hr.
[b]Dose × 10$^6$ rad
[c]0.1M H$_2$SO$_4$.
[d]Graft confirmed by microanalysis.
Note:
Examples 3 and 5 given by way of comparison only.

Table 3 shows the results of Gamma ray grafting of p-styryl diphenyl phosphine to P.V.C. film.

TABLE 3

Gamma Ray Grafting of p-Styryl Diphenyl Phosphine to PVC Film

| Dose (M rad) | Graft (%) |
|---|---|
| 1.5 | 29 |
| 3.4 | 32 |
| 4.9 | 38 |

Solvent: dioxam/methanol (3/2 v/v); Monomer conc. 14% (w/v). Dose rate 21 kilorad/hr.

In the heterogenisation studies recorded in Table 4 the significant feature of the results is not only the reactivity of the copolymerised p-styryl diphenyl phosphine in insolubilised form for hydrogenation but also the apparent lack of colour in the supernatant benzene after reaction indicating no significant leaching of the complex from the surface of the monomer-substrate conjugate. In runs 3 and 4 of Table 4 the support was partially charred after the reaction indicating that considerable local heat had been generated during the catalysis reaction.

The hydrogenation conditions used in Table 4 were 0.3 grams of support containing complex were suspended in 2 ml. of solution (16.4 g cyclohexene in 100 ml. benzene) and sealed off with 1 atmosphere of hydrogen from 65 hours at 80° C. without shaking.

TABLE 4

Hydrogenation of cyclohexene with heterogenized homogeneous catalysts using supports in Table 2[a].

| Run | Support | Catalyst | Complex on surface (%) | Conversion (%) of cyclohexene[b] |
|---|---|---|---|---|
| 1 | 2 | Chlorocarbonyltris (triphenyl phosphine) iridum | 1.5 | 29 |
| 2 | 2 | Chlorotris (triphenylphosphine) rhodium (I) | 2.5 | 30 |
| 4 | 4 | Chlorotris (triphenylphosphine) rhodium (I) | 8.0 | 3 |
| 5 | [c] | O | 0 | 0 |

[a]Benzene used to heterogenize catalyst.
[b]Hydrogenation with cyclohexene for 65 hrs at 80 C.
[c]Polystyrene used as blank.

Catalysts according to this invention may be used not only as hydrogenation catalysts but also as catalysts for a wide range of reactions such as esterification, dehydrogenation and hydroformylation.

It is surprising that the bulky diphenyl phosphine group in the monomers does not hinder surface grafting. It is believed that the initial adsorption of monomer on the polymer surface occurs via a $\pi$—complex involving the C=C bond of the monomer.

We claim:

1. A process for the production of a heterogeneous catalyst comprising the steps of:
    (a) irradiating an organic macromolecular substrate or a metal substrate with ionising or ultra violet radiation in the presence of a monomer selected from the group consisting of o-, m-, or p-styryl diphenyl phosphine and o-, m- or p-phenyl acrylyl diphenyl phosphine, to graft the monomer to the substrate, and
    (b) reacting the graft copolymer with a homogeneous catalyst selected from the group consisting of catalytic metal salts and catalytic organometallic complexes such that the monomer-substrate conjugate becomes a ligand of the catalyst.

2. A process as claimed in claim 1 in which the catalytic metal salts and organometallic complexes are metal salts and organometallic complexes containing a metal selected from the group consisting of Ruthenium, Rhodium, Palladium, Osmium, Iridium and Platinum.

3. A process as claimed in claim 1 in which the macromolecular substrate is selected from the group consisting of polyethylene, polypropylene, polystyrene, polyvinyl chloride, cellulose and wool.

4. A process as claimed in claim 1 in which the metal substrate is selected from the group consisting of copper, zinc, aluminium and iron.

5. A process as claimed in claim 1 in which the monomer is p-styryl diphenyl phosphine.

6. A process as claimed in claim 1 in which the monomer is grafted to the substrate using $\gamma$ radiation.

7. A process as claimed in claim 6 in which the $\gamma$ radiation is applied in a dose of from $0.01 \times 10^6$ rad to $10 \times 10^6$ rad at a dose rate of from $0.001 \times 10^6$ rad/hr. to $5 \times 10^6$ rad/hr.

8. A process as claimed in claim 7 in which the dose is from $0.5 \times 10^6$ rad to $5 \times 10^6$ rad and the dose rate is from $0.01 \times 10^6$ rad/hr. to $0.05 \times 10^6$ rad/hr.

9. A process as claimed in claim 1 in which the monomer is grafted to the substrate using U.V. radiation.

10. A process as claimed in claim 9 in which the U.V. radiation is equivalent to that applied from a high pressure 90 W mercury lamp for from 1 to 100 hours with the sample distanced 30 cm. from the lamp.

11. A process as claimed in claim 9 in which a radical forming sensitiser is present while the monomer and substrate are being irradiated.

12. A process as claimed in claim 11 in which the sensitiser is selected from the group consisting of benzoin ethyl ether or biacetyl.

13. A process as claimed in claim 11 in which the sensitiser is present in an amount of from 0.1% to 5% by volume of the reaction mixture.

14. A process as claimed in any one of claim 1 in which the substrate is macromolecular and in that the irradiation is carried out in a solvent capable of swelling the substrate.

15. A heterogeneous catalyst comprising an organic macromolecular substrate or a metal substrate having grafted thereon a monomer selected from the group consisting of o-, m- or p-styryl diphenyl phosphine and o-, m-, or p-phenyl acryl diphenyl phosphine, this monomer-substrate conjugate being a ligand of a homogeneous catalyst selected from the group consisting of catalytic metal salts and catalytic organo-metallic complexes.

16. A heterogeneous catalyst as claimed in claim 15 in which the catalytic metal salts and organometallic complexes are metal salts and organometallic complexes containing a metal selected from the group consisting of Ruthenium, Rhodium, Palladium, Osmium, Iridium and Platinum.

17. A heterogeneous catalyst as claimed in claim 15 in which the macromolecular substrate is selected from the group consisting of polyethylene, polypropylene, polystyrene, polyvinyl chloride, cellulose and wool.

18. A heterogeneous catalyst as claimed in claim 15 in which the metal substrate is selected from the group consisting of copper, zinc, aluminium and iron.

19. A heterogeneous catalyst as claimed in claim 15 in which the monomer is p-styryl diphenyl phosphine.

* * * * *